US00PP19972P2

(12) United States Plant Patent
Zonneveld

(10) Patent No.: US PP19,972 P2
(45) Date of Patent: Apr. 28, 2009

(54) *AGAPANTHUS* PLANT NAMED 'SENNA'

(50) Latin Name: *Agapanthus africanus*
Varietal Denomination: Senna

(76) Inventor: Piet Zonneveld, Beethovenlaan 57, 2215SG Voorhout (NL)

( * ) Notice: Subject to any disclaimer, the term of this patent is extended or adjusted under 35 U.S.C. 154(b) by 0 days.

(21) Appl. No.: 12/154,273

(22) Filed: May 21, 2008

(51) Int. Cl.
*A01H 5/00* (2006.01)

(52) U.S. Cl. ..... Plt./398

(58) Field of Classification Search ..... Plt./398
See application file for complete search history.

*Primary Examiner*—Kent L Bell
(74) *Attorney, Agent, or Firm*—Penny J. Aguirre

(57) ABSTRACT

A new cultivar of *Agapanthus* named 'Senna', characterized by its very tall strong peduncles that are purple-black in color and held erect, its free-flowering habit with umbels of violet blue flowers, and its longevity as a cut flower of 2 weeks.

2 Drawing Sheets

Botanical classification: *Agapanthus africanus*.
Varietal denomination: 'Senna'.

BACKGROUND OF THE INVENTION

The present invention relates to a new and distinct cultivar of *Agapanthus africanus* and will be referred to hereafter by its cultivar name, 'Senna'. 'Senna' represents a new cultivar of lily-of-the-Nile, a perennial grown for landscape and cut flower use.

The new *Agapanthus* originated as the result of self-pollination of *Agapanthus africanus* 'Back in Black' (U.S. Plant Pat. No. 16,244), made by the Inventor, under controlled conditions in a field at his nursery in Hillegom, The Netherlands in 2004. Pollination was done under controlled conditions in which the flower heads were covered to prevent contamination from cross-pollination. 'Senna' was selected as unique from its parent and all other cultivars known to the Inventor in 2006.

Asexual reproduction of the new cultivar was first accomplished by the Inventor by division in 2006 in Hillegom, The Netherlands. Propagation by division and tissue culture has determined that the characteristics of this cultivar are stable and are reproduced true to type in successive generations.

SUMMARY OF THE INVENTION

The following traits have been repeatedly observed and represent the characteristics of the new cultivar. The new *Agapanthus* has not been observed under all possible environmental conditions. The phenotype may vary somewhat with variations in temperature, day-length, light intensity, soil types, and water and fertility levels without, however, any variance in genotype. The general observations, and descriptions that follow describe plants that were grown outdoors in a trial field in Lisse, The Netherlands for a period of one year.

1. 'Senna' exhibits peduncles that are very long, reaching about 90 cm in height.
2. 'Senna' exhibits peduncles that are strong, held primarily upright, and purple-black in color.

3. 'Senna' exhibits umbels of numerous violet blue colored flowers.
4. 'Senna' exhibits a free flowering habit.
5. 'Senna' exhibits flowering stems that last 2 weeks as a cut flower.

In comparison to the parent plant, 'Back in Black', 'Senna' has peduncles that reach 90 cm in height, whereas the peduncles of 'Back in Black' reach 50 cm in height. They are similar in flower color and in having purple-black flower scapes. 'Senna' can be compared to the cultivar 'Helsinki' (not patented), 'Helsinki' is similar in having long peduncles reaching about 100 cm in height however, the peduncles of 'Helsinki' are green in color and the flower color is lighter blue.

BRIEF DESCRIPTION OF THE DRAWING

The accompanying colored photographs illustrate the overall appearance and distinct characteristics of the new *Agapanthus*. The plants in the photographs were taken of a plant of 'Senna' one-year in age as grown outdoors in a 20 cm container.

The photograph on the first sheet illustrates the habit of 'Senna' in bloom and its long peduncles.

The photographs on the second sheet provide a close-up view of an inflorescence (top) and leaves (bottom) of 'Senna'.

The colors in the photographs are as close as possible with the photographic and printing technology utilized. The color values cited in the detailed botanical description accurately describe the colors of the new *Agapanthus*.

DETAILED BOTANICAL DESCRIPTION

The general observations and descriptions describe plants one year-old in age as grown outdoors under field conditions in Hillegom, The Netherlands. The plants were grown with average day temperatures of 12° to 30° C. and average night temperatures of 5° to 16° C. under ambient light. The color determinations are in accordance with the 2001 RHS Colour Chart of the Royal Horticultural Society, London, England, except where general color terms of ordinary dictionary significance are used.

General description:

*Blooming period.*—July to August in The Netherlands.

*Plant habit.*—Deciduous, clump-forming basal rosettes with tall upright peduncles.

*Height and spread.*—Reaches a height of about 96 cm in bloom with foliage height of about 29 cm and a spread of about 41 cm.

*Cold hardiness.*—At least to U.S.D.A. Zone 8.

*Diseases and pests.*—No susceptibility or resistance to diseases or pests has been observed.

*Root description.*—Thick, fleshy, freely branched.

Growth and Propagation:

*Propagation.*—Tissue culture and division.

*Growth rate.*—Moderately vigorous, leaf length increases about 5 cm per month with peduncles growing about 4 cm a day once they emerge.

Foliage description:

*Leaf shape.*—Linear.

*Leaf division.*—Simple.

*Leaf base.*—Cuneate.

*Leaf arrangement.*—2-ranked, in rosette.

*Leaf apex.*—Acute.

*Leaf aspect.*—Emerging leaves erect, then cascade.

*Leaf venation.*—Parallel, a color upper surface 137B and 144A near base, color lower surface 144A.

*Leaf margins.*—Entire.

*Leaf size.*—Average of 26.2 cm in length and 2.1 cm in width.

*Leaf surface.*—Glabrous, slightly glossy.

*Leaf substance.*—Thick and leathery, moderate to high durability to stress.

*Leaf number.*—Average of 8 per rosette.

*Leaf color.*—Young leaves, upper surface; 143A, young leaves, lower surface; 143B to 143C, mature leaves, upper surface; 137B and 144A near base, mature leaves, lower surface; 137B to 137C and 144A to 144B near base.

*Leaf attachment.*—Sessile to crown.

Flower description:

*Inflorescence type.*—Simple umbel.

*Flower fragrance.*—None.

*Flower type.*—Campanulate, apetalous.

*Flower number.*—An average of about 55 flowers per umbel, one umbel per peduncle and one peduncle per rosette.

*Inflorescence size.*—Average of 10.5 cm in depth and 15.5 cm in diameter.

*Rate of flower opening.*—From 15 to 30% are open at one time.

*Flower size.*—About 3.3 cm in depth and 2.5 cm in width.

*Lastingness of flower.*—About 7 days, persistent.

*Longevity as a cut flower.*—About 2 weeks.

*Flower aspect.*—Held slightly downward from pedicel.

*Peduncle.*—Strong, somewhat flattened, held erect, average of 90 cm in length and 1.2 cm in width at distal region and 7 mm in width at proximal region, surface is glabrous, color slightly more purple than 202A with dots a color between 143A and 144A with base is a color between 143A and 144A with dots slightly more purple than 202A.

*Pedicels.*—Strong, average of 5.2 cm in length and 1.5 mm in width, held erect to horizontal, color is slightly more purple than 202A, surface is glabrous.

*Flower buds.*—Obovate in shape, average of 2.6 cm in length and 7 mm in width, color is 93A with stripes N89A and base N89A.

*Tepals.*—6 to 8, fused at base (lower 30%), narrow obovate in shape, entire margin, glabrous texture, broadly acute apex, average of 3.3 cm in length and 7 mm in width, color when opening inner surface; 93C with longitudinal stripes slightly lighter than 93A, color when opening outer surface; N89C with stripes N89A and base N89A, color fully open inner surface; 93C with stripes slightly lighter than 93A, color fully open outer surface N89A with stripes and base N89A.

Reproductive organs:

*Gynoecium.*—1 Pistil, average of 1.6 cm in length, stigma is narrow clavate in shape and 92D in color, style is about 1.55 cm in length and 92B to 92D in color, ovary is 150B to 150C in color.

*Androcoecium.*—6 stamens, anthers are dorsified, oblong in shape, average of 2 mm in length, and 92A to 92C in color, filament is 1.5 cm in length, pollen is low in quantity and 151C in color.

*Fruit/Seed.*—Seed production has not been observed.

It is claimed:

1. A new and distinct cultivar of *Agapanthus* plant named 'Senna' as herein illustrated and described.

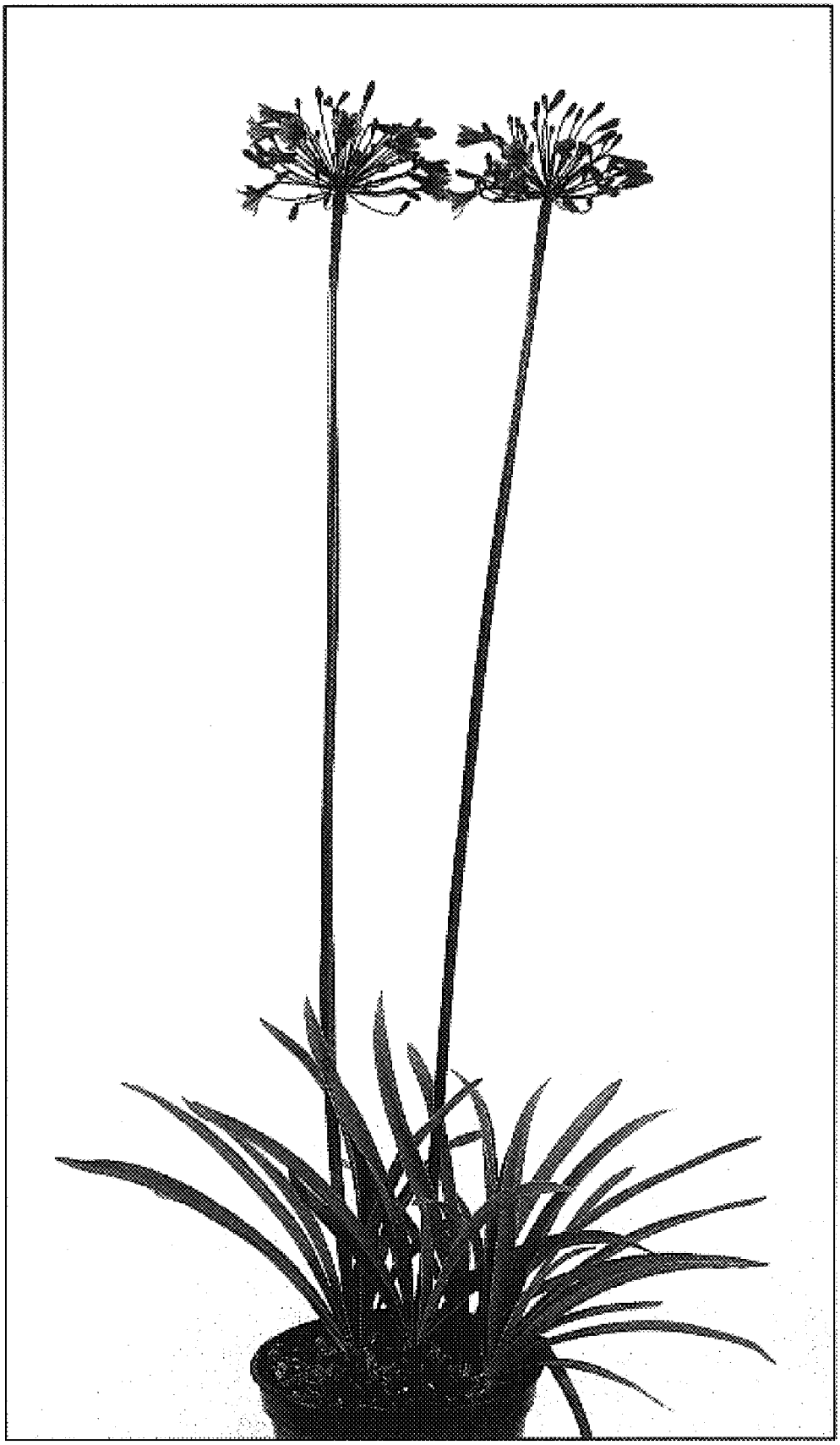

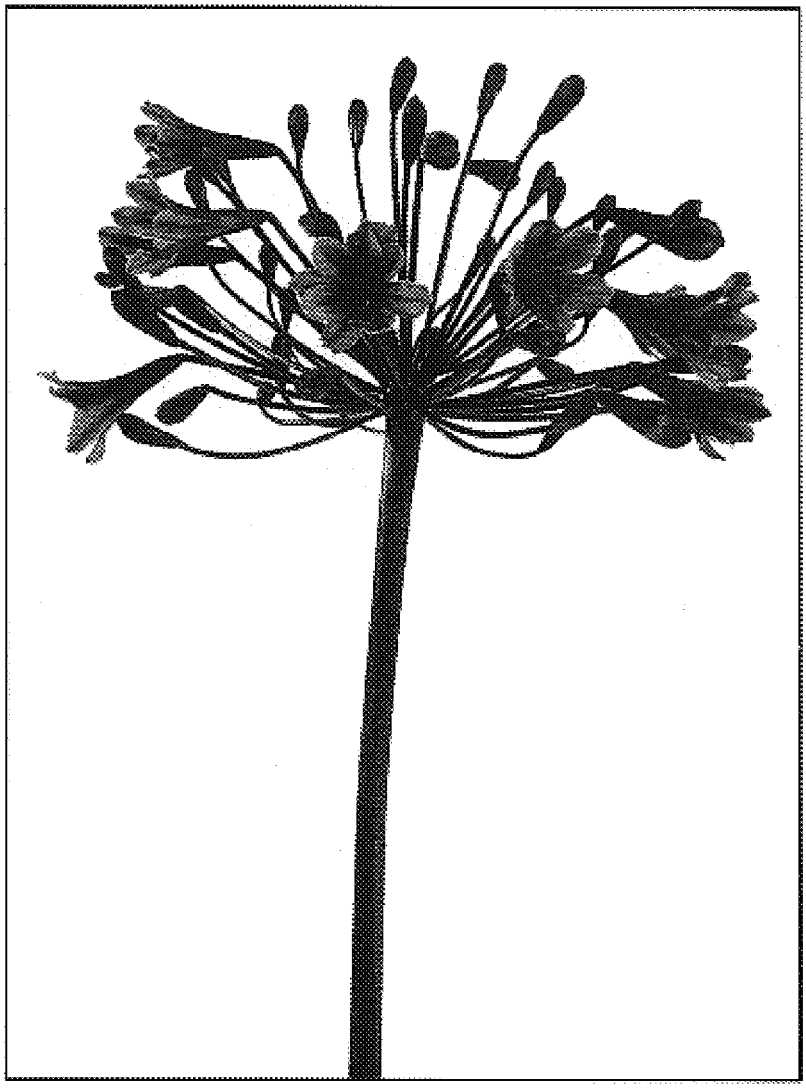
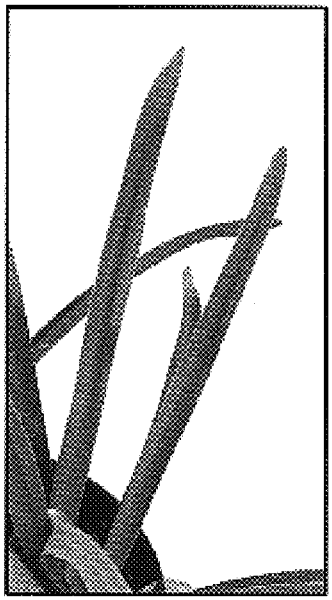

* * * * *